United States Patent
MacMahon

(10) Patent No.: US 11,247,067 B2
(45) Date of Patent: Feb. 15, 2022

(54) APPARATUS AND METHODS FOR PHOTOTHERAPY

(71) Applicant: Chine, LLC, Exeter, NH (US)

(72) Inventor: John MacMahon, Exeter, NH (US)

(*) Notice: Subject to any disclaimer, the term of this patent is extended or adjusted under 35 U.S.C. 154(b) by 0 days.

(21) Appl. No.: 17/199,068

(22) Filed: Mar. 11, 2021

(65) Prior Publication Data

US 2021/0283420 A1    Sep. 16, 2021

Related U.S. Application Data

(60) Provisional application No. 62/988,138, filed on Mar. 11, 2020.

(51) Int. Cl.
*A61N 5/06*    (2006.01)

(52) U.S. Cl.
CPC .... *A61N 5/0613* (2013.01); *A61N 2005/0632* (2013.01); *A61N 2005/0643* (2013.01); *A61N 2005/0661* (2013.01)

(58) Field of Classification Search
CPC .......... A61N 5/0613; A61N 2005/0643; A61N 2005/0632; A61N 2005/0661
See application file for complete search history.

(56) References Cited

U.S. PATENT DOCUMENTS

| | | | |
|---|---|---|---|
| 4,998,931 | A | 3/1991 | Slichter et al. |
| 8,109,981 | B2 | 2/2012 | Gertner et al. |
| 10,300,299 | B2 | 5/2019 | Bourke, Jr. et al. |
| 2009/0228080 | A1 | 9/2009 | Kwon et al. |
| 2009/0233999 | A1 | 9/2009 | Heaton et al. |
| 2010/0121420 | A1 | 5/2010 | Fiset et al. |
| 2015/0025601 | A1 | 1/2015 | Fiset |
| 2016/0129279 | A1 | 5/2016 | Ferolito |

(Continued)

FOREIGN PATENT DOCUMENTS

| | | |
|---|---|---|
| KR | 20170058958 A | 5/2017 |
| WO | 9010461 | 9/1990 |

(Continued)

OTHER PUBLICATIONS

English translation of KR20170058958A.

(Continued)

*Primary Examiner* — Rex R Holmes
(74) *Attorney, Agent, or Firm* — Law Office of Alan W. Cannon

(57) ABSTRACT

Apparatus and methods of controlled therapeutic modulation of an immune response by an immune system of a patient. UV radiation is applied to the skin of a patient for a predetermined time period or dose. The application of UV radiation is repeated for the predetermined time or dose or for a modified predetermined time period or dose based on patient feedback after applying for the predetermined time period or dose, multiple times, wherein each repetition is performed after a predetermined rest period has passed. The patient is tested after at least one session of application of UV radiation and levels of one or more indicators read by the test are compared to levels that were established as baseline levels from a test taken before the initial application of UV radiation. The treatments are discontinued when a predetermined differential threshold between retesting levels and baseline levels in at least one indicator has been met, or for a predetermined number of times, whichever occurs first.

15 Claims, 8 Drawing Sheets

(56) References Cited

U.S. PATENT DOCUMENTS

| | | |
|---|---|---|
| 2019/0168016 A1 | 6/2019 | Anderson et al. |
| 2020/0121943 A1 | 4/2020 | Anderson et al. |
| 2020/0215215 A1 | 7/2020 | Randers-Pehrson et al. |
| 2020/0261608 A1 | 8/2020 | Crosby et al. |

FOREIGN PATENT DOCUMENTS

| | | |
|---|---|---|
| WO | 02053231 | 11/2002 |
| WO | 2008136958 | 11/2008 |

OTHER PUBLICATIONS

English translation of WO02053231.

Elmets et al., "Joint American Academy of Dermatology National Psoriasis Foundation guidelines of care for the management and treatment of psoriasis with phtotherapy", J Am Acad Dermatol Sep. 2019 pp. 775-804.

Flynn et al., "Elevated Inflammatory Status and Increased Risk of Chronic Disease in Chronological Aging: Inflamm-aging or Inflamm-inactivity?", Aging and Disease, vol. 10, No. 1, pp. 147-156, Feb. 2019.

Hashimoto et al., "Narrow-Band Ultraviolet B Phototherapy Ameliorates Acute Graft-Versus-Host Disease of the ntestine by Expansion of Regulatory T Cells", PLOS ONE, Mar. 31, 2016, pp. 1-16.

Holick et al., "The D-lemma: narrow-band UV type B radiation versus vitamin D supplementation versus sunlight for cardiovascular and immune health", Am J Clin Nutr, 2017:105, pp. 1031-1032.

Huang et al., "Clinical features of patients infected with 2019 novel coronavirus in Wuhan, China", Lancet, vol. 395, Feb. 15, 2020, pp. 497-506.

Huang et al., "An Interferon-gamma-Related Cytokine Storm in SARS Patients", J Med Virol, 75:185-194; 2005.

Iyama et al., "Narrowband ultraviolet B phototherapy ameliorates acute graft-versus-host disease by a mechanism involving in vivo expansion of CD4+CD25+Foxp3+regulatory T cells", Int J Hematol, Apr. 2014, Abstract.

Johnson-Huang et al., "Effective narrow band ultravioloet B radiation therapy suppresses the IL-23/IL-17 axis in normalized psoriasis plaques", J Invest Dermatol, Nov. 2010; 130(11), 2654-2663.

Kreutz et al., "Whole-Body UVB Irradiation during Allogeneic Hematopoietic Cell Transplantation is Safe and Decreases Acute Graft-versus-Host Disease", J Invest Dermatol, Jan. 2012; 132(1): 179-187.

"LED Light Therapy for Skin: What to Know", Healthline, Apr. 5, 2019; pp. 1-36.

Marquez et al., "Sexual-dimorphism in human immune system aging", Nature Communications, 2020 11 751; pp. 1-17.

Ponda et al., "A randomized clinical trial in vitamin D-deficient adults comparing replenishment with oral vitamin D3 with narrow-band UV type B light: effects on cholesterol and the transcriptional profiles of skin and blood", Am J Clin Nutr 2017;105; pp. 1230-1238.

Sigman et al., "A 57-Year-Old African American Man with Severe COVID-19 Pneumonia Who Responded to Supportive Photobiomodulation Therapy (PBMT): First Use of PBMT in COVID-19", Am J Case Rep Aug. 7, 2020; 21_pp. 1-7.

Tembhre et al., "T helper and regulatory T cell cytokine profile in active, stable and narrow band ultraviolet B treated generalized vitiligo", Clinica Chimica Acta vol. 424, Sep. 23, 2013; Abstract.

Treister et al., "Narrow-band UVB phototherapy for management of oral chronic graft-versus-host disease", Photodermatol Photoimmunol Photomed Mar. 31, 2015; Abstract.

APPARATUS AND METHODS FOR PHOTOTHERAPY

CROSS-REFERENCE

This application claims the benefit of U.S. Provisional Application No. 62/988,138, filed Mar. 11, 2020, which application is incorporated herein, in its entirety, by reference thereto.

FIELD OF THE INVENTION

The field of the invention relates to phototherapy, more particularly to UV energy therapy applied to the skin to elicit a photo immune response.

BACKGROUND OF THE INVENTION

Phototherapy has been used for treatment of a larger variety of cutaneous diseases, including psoriasis, atopic dermatitis, vitiligo, mastocytosis, pruritus and early-stage cutaneous T-cell lymphoma, see Zizi et al., "How it Works: The Immunology Underlying Phototherapy", Deramatol Clin 38 (2020)-53. However, a method to optimize a photoimmune response into a systemic immune therapy has not been described.

The dysregulation of the immune system is age and sex dependent and is documented with men reaching an inflection point at around 63 years old and women at around 68 years old, which reflects upon the life span differences between the sexes during which the immune system undergoes more abrupt epigenomic changes representing age and sex dependent risk profile for susceptibility to manage additional acute and chronic immune responses. (Marquez et al., "Sexual-dimorphism in human immune system aging", Nat Commun 11, 751 (2020)).

Cardiovascular disease, type 2 diabetes, cognitive disorders, such as dementia and Alzheimer's, and osteoporosis, to name a few, are known to be exacerbated by a poorly regulated innate immune system. Inflammatory dysregulation and immune frailty is considered as a driver of baseline inflammation associated with age, and in studies of 90 and 100 year old people, a healthy immune regulation system is a strong predictor of survival, "establishing a healthy balance of pro- and anti-inflammatory biomarkers that may delay the progression of inflamm-aging and its related morbidities in this unique population." (Flynn et al., "Elevated Inflammatory Status and Increased Risk of Chronic Disease in Chronological Aging: Inflamm-aging or Inflamm-inactivity?", Aging and Disease, Volume 10, Number 1, February 2019).

There is a need to improve the quality of life and survival of people by assisting/correcting the regulatory response of those where a dysregulated immune system is driving clinical presentations including slowly presenting conditions, such as, but not limited to, cardiovascular, cognitive decline and acute settings including stroke, GVHD and the cytokine release system and the subsequent cytokine storm associated with coronavirus.

SUMMARY OF THE INVENTION

According to an aspect of the present invention, a method of controlled therapeutic modulation of an immune response by an immune system of a patient is provided. The method includes: testing patient biological feedback to establish a baseline level of one or more indicators of immune regulation; applying UV radiation to skin of the patient for a predetermined time period or dose; repeating the applying step for the predetermined time period or dose, or for a modified predetermined time period or dose based on patient feedback after the applying for the predetermined time period or dose, multiple times, wherein each repeating treatment is performed after a predetermined rest period; retesting the patient after at least one session of applying UV radiation; comparing levels of the one or more indicators determined in the retesting to levels established as the baseline levels; discontinuing the repetition of the applying step for the predetermined or modified predetermined time period or dose when a predetermined differential threshold between the retesting levels and the baseline levels in at least one of the indicators has been met; as the dose of UV radiation is geometry dependent between patient and UV source, geometric sensors are also considered biological feedback; and further repeating the applying step for the predetermined time period or dose or modified predetermined time period or dose when the differential threshold has not been met, the further repeating steps being carried out until the differential threshold has been met, or for a predetermined number of times, whichever occurs first.

In at least one embodiment, the indicators include T-cells and cytokines.

In at least one embodiment, the indicators include temperature, heart rate, and blood oxygen levels.

In at least one embodiment, the biological feedback includes non-contacting sensors to include at least one of patient, temperature, UV source to patient geometry, ballistic heart rate, respiration rates.

In at least one embodiment, the testing further includes testing for a Vitamin D level.

In at least one embodiment, the indicators comprise inflammatory markers including at least one of CRP, LDH and ferritin, and wherein the method further comprises discontinuing repeating the applying step for the predetermined time or dose or modified predetermined time or dose when a predetermined differential threshold between a retesting level of at least one of the inflammatory markers and the baseline level of the at least one of the inflammatory markers has been met.

In at least one embodiment, the applying UV radiation comprises applying UVB radiation.

In at least one embodiment, the applying UV radiation comprises applying a combination of UVC and UVB radiation.

In at least one embodiment, the applying UV radiation comprises applying NB-UVB radiation.

In at least one embodiment, the wavelengths of UV radiation applied are restricted to NB-UVB radiation.

In at least one embodiment, the patient is infected with a coronavirus, such as COVID-19, and the method is applied to improve outcomes for the coronavirus/COVID-19 patient.

In at least one embodiment, the patient is infected with sepsis and the method is applied to improve outcomes for the sepsis patient.

In at least one embodiment, the method is applied to the patient in an acute setting.

In at least one embodiment, the patient has cognitive dysfunction, as in dementia and Alzheimer's.

In at least one embodiment, the method is applied to the patient in an intensive care unit (ICU).

In at least one embodiment, the method includes integrated source of UV radiation and at least one non-contacting biological feedback sensor, such as, but not limited to geometric sensors and/or but not limited temperature sensors.

In another aspect of the present invention, a stand-alone, self-sterilizing phototherapy apparatus is provided that includes: an application head configured to apply UV radiation to skin of a patient to affect controlled therapeutic modulation of an immune response by an immune system of the patient; a housing; an articulating arm mounted at one end in the housing and at an opposite end to the application head; a power source; and a processor, powered by the power source and configured to control application of the UV radiation to the skin of the patient via the application head, and to control application of UV radiation to the apparatus to perform self-sterilization.

In at least one embodiment, the housing is configured to receive the articulating arm and the application head therein upon controlling the articulating arm to deliver the application head into the housing; the housing further comprising a lid configured to be closed over the application head and articulating arm once fully received in the housing; wherein inner walls of the housing and lid are mirrored; and wherein application head and the inner walls are positioned so that controlling the application head to emit UV radiation when inside of the closed housing reflects the UV radiation so that it is applied to all surfaces of the application head and articulating arm for sterilization of the same.

In at least one embodiment, the housing is configured to receive the articulating arm and the application head therein upon controlling the articulating arm to deliver the application head into the housing; the housing further comprising inner walls and outer walls connected together and translatable so that the inner walls can be translated to occupy positions of the outer walls and vice versa; wherein the inner walls and the outer walls comprise mirrored surfaces; wherein application head is positioned so that controlling the application head to emit UV radiation when inside of the housing reflects the UV radiation so that it is applied to all surfaces of the application head and articulating arm for sterilization of the same and to all surfaces of the inner walls; and wherein the outer walls are translated to locations inside the housing and are sterilized, so that both inner and outer walls of the housing are sterilized by application of UV energy from the application head when in a position within the housing.

In at least one embodiment, the housing further includes a lid configured to be closed over the application head and articulating arm once fully received in the housing; wherein the lid comprises an inner wall and an outer wall connected together and that are translatable so that the inner wall can be moved to a position of the outer wall and vice versa, and wherein the outer wall of the lid is translated to a location inside the housing and is sterilized, so that both inner and outer walls of the lid are sterilized by application of UV energy from the application head when in a position within the housing.

In at least one embodiment, the processor is further configured to control application of the UV radiation to external surfaces of the housing to perform self-sterilization.

In at least one embodiment, the apparatus is configured to emit UVB radiation.

In at least one embodiment, the apparatus is configured to be alternately controlled to emit UVB radiation or UVC radiation.

In at least one embodiment, the apparatus is configured to emit NB-UVB radiation.

In at least one embodiment, the apparatus integrates a method of application of UV radiation to a patient and a method of biological feedback obtained from the patient resulting from the application of UV radiation, to modify or discontinue a following application of UV radiation to the patient.

In at least one embodiment, the apparatus is configured to treat patients with infectious diseases, such as COVID-19, wherein the apparatus is configured to apply the UV radiation to the skin of the patient in a location overlying the lungs of the patient, and wherein the patient is infected with the infectious disease such as COVID-19.

According to an aspect of the present invention, a method of treating a patient with phototherapy includes: providing a stand-alone, self-sterilizing phototherapy apparatus comprising an application head configured to apply UV radiation to skin of a patient to affect controlled therapeutic modulation of an immune response by an immune system of the patient; a housing; an articulating arm mounted at one end in the housing and at an opposite end to the application head; a power source; and a processor, powered by the power source and configured to control application of the UV radiation to the skin of the patient via the application head, and to control application of UV radiation to the apparatus to perform self-sterilization; applying UV radiation from the application head to the skin of the patient for a predetermined time to provide a predetermined dosage of radiation; and applying UV radiation from the application head to the apparatus for a predetermined time to sterilize the apparatus.

In at least one embodiment, the providing includes remotely driving the apparatus to the location of the patient, so that the operator does not need to be at the location of the patient; and wherein the applying UV radiation to the skin and the applying UV radiation to sterilize are also performed at the location of the patient, remote from an operator of the apparatus.

In at least one embodiment, the UV radiation is applied to the skin at a location overlying tissues to be treated.

In at least one embodiment, the UV radiation is applied to the skin overlying at least a portion of the lungs and the patient has been diagnosed with COVID-19.

In at least one embodiment, the UV radiation applied to the skin is UVB radiation and the radiation applied to the apparatus is UVB radiation.

In at least one embodiment, the UVB radiation applied to the skin is NB-UVB radiation.

In at least one embodiment, the UV radiation applied to the skin is UVB radiation and the radiation applied to the apparatus is UVC radiation.

In at least one embodiment, the UVB radiation applied to the skin is NB-UVB radiation.

These and other advantages and features of the invention will become apparent to those persons skilled in the art upon reading the details of the methods, systems and apparatus as more fully described below.

DETAILED DESCRIPTION OF THE INVENTION

Figure 1:
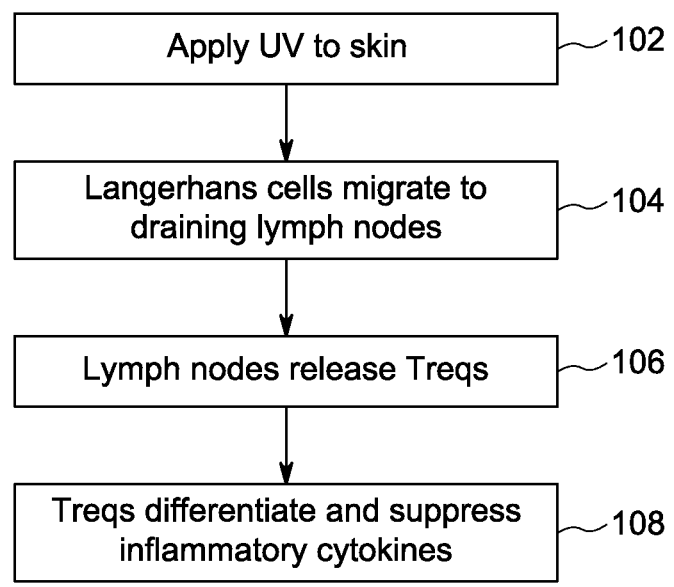
FIG. 1 illustrates events that may occur as a result of UV host-directed therapy to the skin of a patient according to an embodiment of the present invention.

Before the present apparatus and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a test" includes a plurality of such tests and reference to "the indicator" includes reference to one or more indicators and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

According to an aspect of the present invention, phototherapy can be used to communicate with the immune system of a patient to regulate, modulate or resynchronize the immune system that has been dysregulated by any of a variety of factors. Such therapy does not result in a systemic suppression of the immune system like what occurs with certain prescription drugs used for immune therapy, but rather a resynchronization of the immune system, thus providing a novel therapy that would not increase a patient's risk of coming down with tuberculosis or other bacterial or viral infections that can gain hold more easily when the immune system is suppressed.

One aspect of the present invention involves the application of UV radiation as a host-directed therapy that initiates a photo-immune response within the lymphatic system of a patient to broadly improve immune regulation. The application of UV radiation to the skin of the patient initiates a cascade that engages the lymphatic system to produce and release regulatory T cells (TRegs) that suppress activation, proliferation, and production of cytokines. The lymphatic system also regulates immune cells (lymphocytes, monocytes, and antibody producing cells called plasma cells). FIG. 1 illustrates events that may occur as a result of UV host-directed therapy to the skin of a patient according to an embodiment of the present invention where the clinical goal is to suppress an over reactive immune system. In patients with dysregulation with suppressed immunity, application of UVB can influence the immune system to correct the imbalance posed by the suppressed immunity and correct the dysregulation, thus allowing the immune system to reach an equilibrium, whether it is correcting from a hyper-inflammatory imbalance or a hypo inflammatory imbalance. At event 102 ultraviolet (UV) radiation is applied to the skin of the patient being treated at an intensity, wavelength and duration to initiate the photo-immune cascade. In response to this, the morphology and function of Langerhans cells are altered, as they migrate from the skin to draining lymph nodes at event 104 and may serve as immune-regulatory cells for immune balance.

In response to this migration, the lymph nodes release regulatory T-cell (TRegs) at event 106. The TRegs differentiate and suppress inflammatory cytokines, see event 108, such as by differentiating to Effector T-Cells, Dendritic cells, etc. The net immune impact of this cascade is to down-regulate inflammation, up-regulate anti-inflammation and to recruit T-cells (TRegs) to carry out immune regulation.

UV energy having wavelengths in a range from 250 nm to 400 nm may be used. Preferred bandwidths of UV energy to be applied are UVB (290 nm to 320 nm), even more preferably NB-UVB (308 nm to 315 nm). NB-UVB may induce different immunological features from broadband ultraviolet B (UVB) and may be more effective for driving the photo-immune cascade described with reference to FIG. 1.

Any of the apparatuses described herein may include treatment by delivery of UV light by applying effective doses of UV light to the skin of a patient. The application of UV light may be on a location of the skin of the patient that overlies tissues most affected by a disease that is being treated. For example, in the case of a patient being treated for coronavirus or COVID-19, the UV light may be applied to the skin covering the chest of the patient in locations overlying the lungs, from the front side of the patient, from the back side of the patient, or from both front and back sides, sequentially or simultaneously.

From guidelines published by the American Academy of Dermatology, the initial doses may range from 300 to 800 mJ/cm$^2$. [Elmets C A, Lim HW, Stoff B, et al. Joint American Academy of Dermatology-National Psoriasis Foundation guidelines of care for the management and treatment of psoriasis with phototherapy. J Am Acad Dermatol. 2019 September; 81(3):775-804. doi: 10.1016/j.jaad.2019.04.042. Epub 2019 Jul. 25. Erratum in: J Am Acad Dermatol. 2020 March; 82(3):780.]. The dosage of a treatment session can be calculated by the intensity of the UV light applied multiplied by the time over which the UV light is applied. UV light may be applied to the skin over a period between 0.01 second and 1 hour. For example, the UV light may be applied for between 0.01 second and about x seconds, where x is 0.1 seconds, 0.5 seconds, 1 second, 2 seconds, 3 seconds, 4 seconds, 5 seconds, 6 seconds, 7 seconds, 8 seconds, 9 seconds, 10 seconds, 12 seconds, 15 seconds, 20 seconds, 25 seconds, 30 seconds, 35 seconds, 40 seconds, 45 seconds, 50 seconds, 55 seconds, 60 seconds, 1 minute, 1.5 minutes, 2 minutes, 2.5 minutes, 3 minutes, 3.5 minutes 4 minutes, 4.5 minutes, 5 minutes, 5.5 minutes, 6 minutes, 6.5 minutes, 7 minutes, 7.5 minutes, 8 minutes, 9 minutes, 10 minutes, 12 minutes, 15 minutes, 20 minutes, 25 minutes, 30 minutes, 35 minutes, 40 minutes, 45 minutes, 50 minutes, 55 minutes, 1 hour, etc. For examples, durations between about 1 minute and 10 minutes, between 2 minutes and 8 minutes, between 3 minutes and 7 minutes may be preferred, between about 4 minutes and 6 minutes may be preferred, etc.

The UV light is preferably applied continuously over the time duration of treatment, but, alternatively, could be applied in a non-continuous (e.g., pulsing, period, etc.) manner. For example, the UV light may be applied at an on/off frequency of between 10 kHz and 1 Hz, such as between about 10 kHz and 1 kHz, between about 1 kHz and 0.1 kHz, between about 1 kHz and 0.5 KHz, between about 1 kHz and 10 Hz, etc. Further, the intensity of the UV light may be constant or varying, but is preferably constant.

The UV light is preferably applied in a plurality of treatment sessions, but could alternatively be applied as a single treatment. For example, the UV light treatment may be applied repeatedly, once every x time units, for a total of y treatments (or less than y treatments if testing determines that the immune response has been satisfactorily achieved prior to y treatments). For example, sessions may be carried out where x is 1 hour, 4 hours, 8 hours, 12 hours, 24 hours, 2 days, 3 days, 1 week, 1 month, 3 months, 6 months, 9 months, 1 year, etc., and y is 2, 3, 4, 5, 6, 7, 8, 9, 10, 11, 12, 20 or more. Some preferred examples, include x as 12 hours or 24 hours and y in the range of 2 to 12, 4 to 10 or 5 to 9.

Ultraviolet light phototherapy devices according to the present invention have the capability of delivering noninvasive UV (preferably UVB, more preferably NB-UVB) as a host-directed immune-modulating therapeutic for patients in acute care settings, including the intensive care unit (ICU) of a hospital. This phototherapy activates an immune response, as discussed generally above, and thus provides the patient with acute, broad immune suppression with fewer, if any, side effects compared to treatment with immune suppressing drugs or other known treatments. The phototherapy induces the lymphatic system to reduce inflammatory cytokines (Th1), increase anti-inflammatory cytokines (Th2), and increase regulatory T cells (Tregs). Th1, Th2 and Tregs are all a part of a larger group of immune system biomarkers. A consequence of these immune actions may result in patients' signatory recovery of temperature, blood oxygen levels and/or heart rate.

In at least one embodiment, NB-UVB is applied by a device as a host-directed immune-modulating therapeutic to a patient infected with COVID-19. As noted, this treatment can be applied even in acute care settings, including the ICU. The value of NB-UVB phototherapy is it provides patients acute broad immune suppression with fewer, if any, side effects compared to treatment with other proposed COVID-19 drugs pre- or post-exposure prophylactic therapeutics.

The application of NB-UVB to the COVID-19 infected patient may indirectly inhibit the coronavirus lifecycle with immunomodulation as the mechanism of action, modifying lung and macrophage pathology. In its most severe form, Severe Acute Respiratory Syndrome Coronavirus 2 (SARS-CoV-2), the virus that causes coronavirus disease 2019 (COVID-19), can lead to life-threatening pneumonia and acute respiratory distress syndrome (ARDS). COVID-19 does not kill; rather, the cytokine storm that can result in response to a COVID-19 infection can be the cause of death. In such an instance, the cytokine storm can induce an unbalanced and hyper-activated immune system which causes potentially fatal swelling and fluid retention in the lungs especially for those COVID-19 patients with co-morbidities. The patient populations most at risk of death or serious complications from a COVID-19 infection typically have unregulated immune systems in common. Vitamin D3 deficiency is a known biomarker for poor immune regulation and is common amongst these high-risk pre-existing conditions. Common levels patient of 25(OH)D hydroxyvitamin D, Critical Deficiency (<20 ng/ml); and insufficiency (<30 ng/ml), for the active form, 1,25-dihydroxyvitamin D insufficiency is (at or below 18 pg/ml).

One of the strongest predictors of outcomes in COVID-19 patients is their level of vitamin D at the time of presentation. Patients with a low level of vitamin D are more susceptible to getting the coronavirus and having bad outcomes from the coronavirus. However the correlation with Vitamin D or Vitamin D3 does not appear to be a direct one, as ingestion of Vitamin D supplements has not consistently resulted in improved outcomes with patient's suffering from coronavirus symptoms. It is believed by the present applicants that the Vitamin D level of a patient with COVID-19 or other disease such as hypertension, cardiovascular disease is indirectly related to the susceptibility to such diseases, as being directly related to the regulation of the immune system as discussed herein.

UV phototherapy, and particularly NB-UVB therapy also raises Vitamin D through its own isomeric channel. The body has evolved to use the highest energy wavelengths that reach the earth as a source of fuel for two parallel but independent processes. Immune health through the photo-immune cascade is one. The other independent process is the thermal isomerization of pre-vitamin D. Since both processes use the same fuel they are naturally found hand in hand. The evidence-based research will show that these are independent of non-environmental sources of vitamin D, such as oral supplemental vitamin D. In a trial by Ponda et al., patients were randomized to narrow band UVB light from a cabinet of fluorescent light bulbs and the other group was randomized to oral vitamin D supplements. In this trial, both patient groups had improved serum vitamin D, but stabilization of the patients' immune systems was evident and superior only in the NB-UVB patients. This trial confirms that the source of your vitamin D is important and that whenever you use naturally synthesized light, this reunites improved vitamin D with improved immune regulation.

Application of UV light to the skin of a patient results in the UV light interacting with lymphatic vessels which are part of the immune system. This causes a series of reactions which result in the formation of immunity stabilizers and immunity biomarkers. As the process proceeds from the lymphatics to the liver and the kidneys, these immunity stabilizers downregulate inflammation and upregulate anti-inflammation and recruit T cells as part of the immune response. The very endpoint of this immunity cascade is the formation in the liver of active vitamin D, hence the biomarker.

Thus, it is believed that the stimulation of the photo-immune cascade is correlated to improved outlooks and results when treating patients with these diseases, and that the Vitamin D level is indirectly correlated to disease outcome, as being directly correlated to the stimulation of the photo-immune cascade. That is, vitamin D is a marker and found only in parallel to immune stability when sourced from NB-UVB. Success in treating COVID-19 patients with this NB-UVB treatment as an immune-modulating therapeutic for pre- and post-exposure prophylactic treatment may empower expanded indications to other acute respiratory viral diseases as well as moving upstream as a primary treatment to address these common co-morbidities. For example, UV phototherapy as described herein, may be applied to potentially reduce, alleviate or eliminate various non-communicable diseases (hypertension, diabetes, cardiovascular disease, metabolic syndrome) that are associated with low vitamin D plasma levels.

NV-UVB applied as described herein as a host-directed therapeutic specifically targets IFN-γ-producing Th1 cells as well as upstream cytokines IL-12 and IL-23. NB-UVB has also been found to have suppressive effects on additional inflammatory mediators, including IL-10, IL-6, IL-8, and IL-18.

Figure 2:
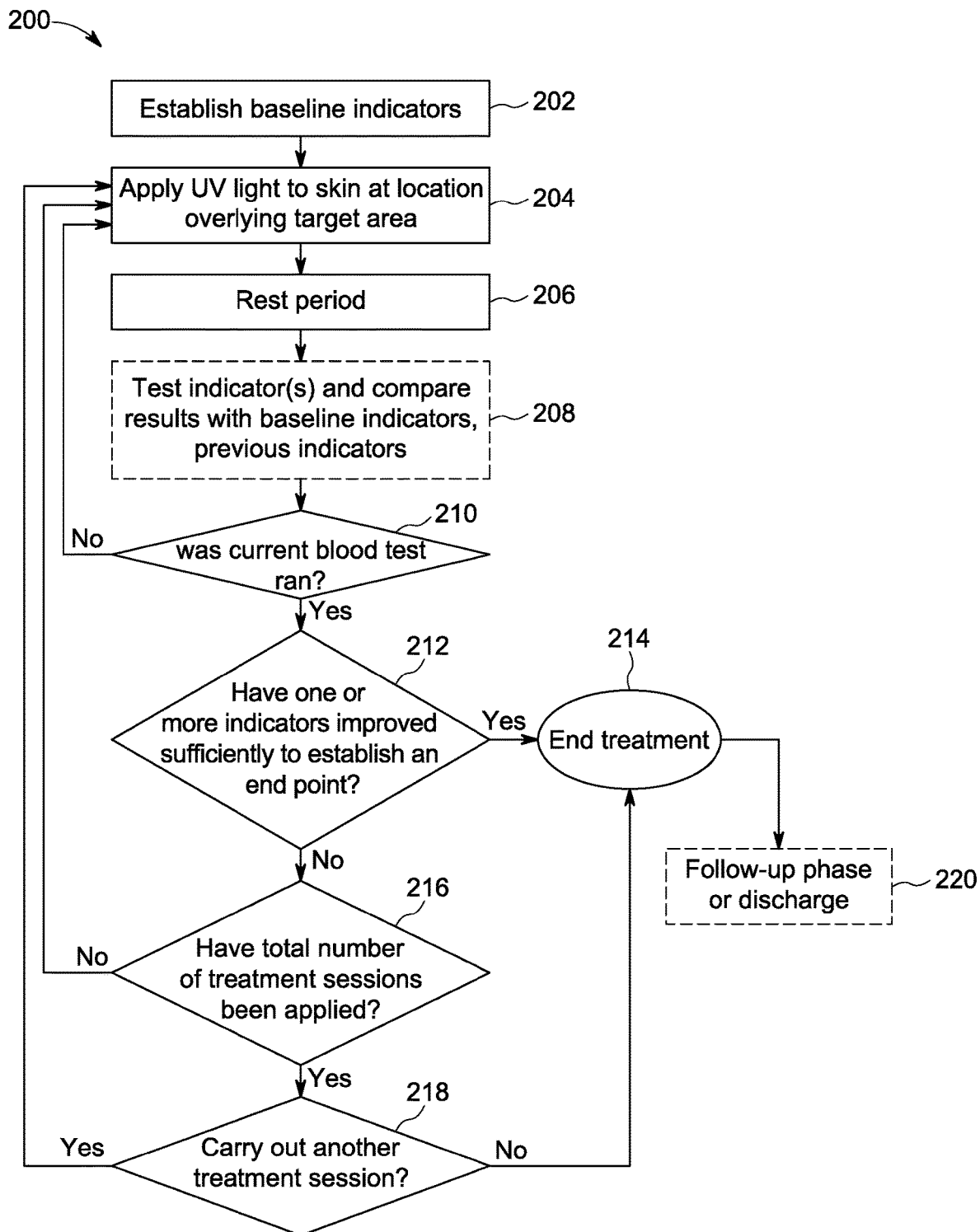
FIG. 2 shows events that may be carried out in a method of phototherapy applied to a patient to improve immune regulation of the patient, according to an embodiment of the present invention.

FIG. 2 shows events that may be carried out in a method 200 of phototherapy applied to a patient to improve immune regulation of the patient, according to an embodiment of the present invention. The patient may be being treated for any number of diseases described herein where an improvement in immune regulation may help the patient to overcome, and more rapidly overcome the ailment experienced. In at least one embodiment the treatment is for a patient having COVID-19. The patient is tested to obtain biological feedback at event 202. For example, a biological assessment, such as a blood sample in this example, is taken from the patient at event 202 to establish baseline indicators against which later blood samples may be tested and compared to indicate improvements resulting from the phototherapy. For example a cytokine panel may be performed where levels of inflammatory cytokines (Th1), anti-inflammatory cytokines (Th2) and regulatory T cells (Tregs) are identified and stored as baseline values. Additional or alternative biomarkers of immune regulation could optionally be performed, such as C-reactive protein (CRP), lactate dehydrogenase (LDH) and/or ferritin. Likewise, the Vitamin D level (e.g., active 1,25 dihydroxyvitamin D) of the blood tested could be identified and stored as a baseline value. Further biological feedback may be additionally or alternatively tested for, such as, but not limited to: the patient's temperature, heart rate and/or blood pressure, which can be taken as stored as baseline values against which to judge improvements.

Once baseline indicators have been established, at event 204 UV light is applied directly to the skin of the patient at a location overlying a target area of the body where an immune response is needed. For example, when treating a patient having COVID-19, where often the lungs are most affected, the UV light can be applied directly to the skin overlying the lungs of the patient, from the front side or from the back side, or from both sides, either sequentially or simultaneously. The UV light is applied at a wavelength or wavelength range, intensity and time duration suitable for stimulating the initiation and continuation of the photo-immune cascade in the patient's body with the goal of increasing both anti-inflammatory cytokines and regulatory T cells and decreasing inflammatory cytokines.

Upon completion of a single treatment at event 204, i.e., after the UV light has been applied to the skin at the desired wavelength(s), intensity(ies) and time(s), application of UV light is discontinued and the patient treatment session ends, with the patient then being allowed a rest or recovery time. During this rest period (event 206), the immune system continues with its response to receiving the application of UV light, where the morphology and function of Langerhans cells are altered, as they migrate from the skin to draining lymph nodes and may serve as immune-regulatory cells for immune suppression. In response to this migration, the lymph nodes release regulatory T-cell (TRegs) that differentiate and suppress inflammatory cytokines, such as by differentiating to Effector T-Cells, Dendritic cells, etc. The net immune impact of this cascade is to down-regulate inflammation, up-regulate anti-inflammation and to recruit T-cells (TRegs) to carry out immune regulation.

The rest period is typically a predetermined rest period and may be any of the time periods described above, e.g., 1 hour, 4 hours, 8 hours, 12 hours, 24 hours, 2 days, 3 days, 1 week, 1 month, 3 months, 6 months, 9 months, 1 year, etc. Alternatively, rest periods between UV light application sessions may vary, but it is preferred to use the same rest period between sessions for each repetition of treatment, and y is 2, 3, 4, 5, 6, 7, 8, 9, 10, 11, 12, 20 or more. Some preferred examples, include x as 12 hours or 24 hours and y in the range of 2 to 12, 4 to 10 or 5 to 9.

After the rest period, at event 208, the patient's blood may optionally be taken to test for one or more of the indicators tested for at event 202, so as to compare the results to see how effective the treatment(s) to date, have been in restoring/improving immune regulation. Additionally, or alternatively, at least one of temperature, blood pressure and/or heart rate can be taken and compared against baseline level(s). Event 208 is indicated as optional, as it may or may not be carried out between each treatment session. For example, for a treatment regimen of 8 treatment sessions, event 208 could be carried out between each of the sessions. Alternatively, event 208 may be carried out after only a subset of the total number of sessions/rest periods. For example, for a treatment regimen planned for 8 treatment sessions, event 208 may be carried out after only the third, fifth and eight treatment session, with event 208 being by passed after the first, second, fourth, sixth and seventh treatment sessions.

At event 210, if a biological marker/indicator, such as, but not limited to a blood test has not been run after the current rest period, then no indicator analysis is performed. Rather another treatment session is carried out as the procedure returns to event 204. On the other hand, at event 210 when a blood test and/or other indicator test such as temperature, blood pressure and/or heart rate and/or other biomarker has been run after the current rest period, the results of the current blood test and/or other indicator are compared with the baseline indicators (and, optionally, any blood test indicators/biomarkers obtained between the current test results and the baseline indicators), to determine whether the immune response/regulation initiated by the treatments has improved one or more of the indicators sufficiently to establish an endpoint of the treatments. For example, an increase in one or more anti-inflammatory cytokines (Th2), regulatory T cells (Tregs) or Vitamin D level by a predetermined percentage, relative to baseline may be determined as an endpoint, e.g., 5%, 10%, 15%, 20%, 25%, 30%, 40%, 50%, 60%, 70%, 75%, 80%, 90%, or 100% or more improvements. Likewise, a decrease in one or more inflammatory cytokines (Th1), C-reactive protein (CRP), lactate dehydrogenase (LDH) and/or ferritin by a predetermined percentage relative to baseline may be determined as an endpoint, e.g., 5%, 10%, 15%, 20%, 25%, 30%, 40%, 50%, 60%, 70%, 75%, 80%, 90%, or 100% or more decrease in level. Additional or alternative improvements sufficient to establish an endpoint include return of the patient's temperature to within a predefined range of normal temperature, e.g., less than 100 degrees F., less that 99.5 degrees F., less than 99 degrees F. or some other predetermined value or range; and/or a return of blood pressure nearer to a predefined normal range and/or a return of heart rate to within a predefined range.

If it is determined at event 212 that an endpoint has been reached, then the treatment sessions for the patient can be discontinued at even 214. Optionally, a follow-up monitoring of the patient can be carried out (event 220), such as for a predetermined period (e.g., 9 to 30 days or more, or until discharge), where additional blood samples can be taken for analysis to determine if immune regulation remains at sufficient levels or if another treatment with UV is indicated. If at event 212 an endpoint has not been reached, then it is determined at event 216 whether the total number of pre-planned (predetermined) treatment sessions have already been applied. If the total number has not yet been reached, then the procedure returns to event 204 where another treatment session of application of UV light to the skin is carried out. If at event 216 it is found that the total number of preplanned sessions has already been performed, then at event 218, a decision is made by the professional(s) treating the patient as to whether to continue with one or more additional treatment sessions. Based on the decision, processing either returns to event 204 or treatment is ended at event 214.

Current UV phototherapy units in use prior to the present invention reside in a dedicated room or facility and are provided access for multiple patients, but the patients must be transported to the dedicated room for treatment. There is an unmet need to deliver UVB to isolated and/or non-ambulatory patients. In this setting sterility is of great importance to reduce exposure for patient to patient transmission of diseases. By providing a relatively small, portable unit for delivery of phototherapy, this expands the range of available treatment settings to areas that have heretofore not been possible, including acute care settings, intensive care units, etc. Mobilization of an apparatus for delivery UVB radiation to a patient, so that the apparatus can be moved to a patient's quarters or bed may be accomplished by a manually-powered or self-powered apparatus, wherein a manually powered apparatus could be provided with wheels or be configured to be placed on a cart with wheels, and pushed to the desired location. A self-powered UV apparatus could be configured with an electric drive motor and battery power source, for example, so that the apparatus could be controlled to drive itself to the desired location. Display 80 could be operated by a health care worker from a location outside of the patient's room, for example. This would provide increased safety to the healthcare worker, particularly for patients having highly contagious diseases, such as COVID-19. By providing the apparatus 30 on a robotic platform to enter the patient's room, orient the apparatus and application head 40, treat the patient, self-sterilize and return to the healthcare worker in a sterilized condition, this would greatly decrease the risk of spreading the disease to the healthcare worker or others outside of the patient's room.

The enhanced care/extension of care to patients that could not previously take advantage of such treatments when they are not able to transport themselves or be transported to a designated room, is further facilitate by self-sterilization features that allow use in settings where sterilization and/or isolation is either convenient or important. Combining these systems with a self-sterilizing component can increase clinical throughput and reduce transmission of disease.

Self-sterilization can be achieved by fluid, energetic or gas delivery. One internally consistent, but not limiting approach is to integrate two spectrums of UV light. UVB for therapy and UVC for sterilization. UVC is commonly known as a sterilizing energy spectrum as independent stand-alone units. However, it is also possible to use UVB radiation to perform sterilization, although the treatment times of radiation to the surface to be sterilized are relatively longer than those required for sterilizing when using UVC. Thus, in an alternative arrangement, UVB can be used for both therapy and sterilization, although the treatment times and intensities/dosages of radiation will vary. Also the frequency/frequency ranges of UVB used for sterilization may be different from those used for treatment.

UVB is commonly delivered in a standing "closet-like form" or as a panel of lights where the patient stands before them for one side and then turns to have other sides provided the light therapy. The vertical presentation of the UVB source is designed to provide an even dose across the subject. In this setting tall vertical bulbs are the source of the UVB. In this setting, but not limited to this design, UVC lights can be placed in the unit as well to be activated for sterilization between clinical UVB treatments. These lights may be delivered in an alternative or other efficient spacing.

For external surfaces, the lights and or external surfaces may rotate to provide surface exposure to the UVC source. The exposed components may also be manufactured from UVC transmitting materials to provide complete surface sterilization from the UVC surfaces. In this embodiment, the complete lights and exposed surfaces are fixed in the cabinet. A further embodiment is the translation of the UVC sources to the relevant surfaces in the form of a rotating gantry or other mechanically controlled translating arm. Another embodiment is provides integrated UVC sources for direct sterile dose.

Confirmation of sterilization can be integrated with terrain mapping of the mechanism surface and dose calculations tracking distance and power output to achieve acceptable dosage.

It is common in the art for UVB to be delivered with bulbs as well as with LED and they are considered in this disclosure to be interchangeable. The vision of tunable bulbs and LEDs is also envisioned in this disclosure.

Another embodiment provides a reflective surface or waveguide to be translated about the surfaces of the unit to distribute coverage of the sterilizing energy.

Figure 3A:
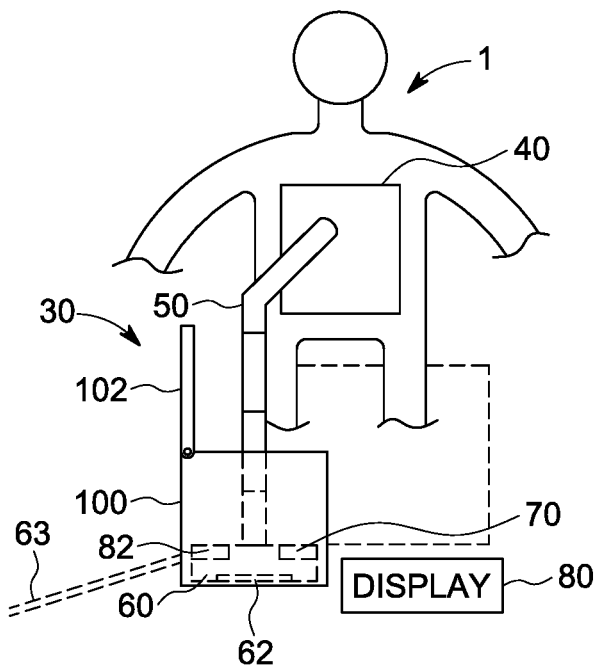
FIG. 3A illustrates a stand-alone, self-sterilizing phototherapy apparatus according to an embodiment of the present invention.

FIG. 3A illustrates a stand-alone, self-sterilizing phototherapy apparatus 30 according to an embodiment of the present invention. Apparatus 30 includes an application head 40 configured to apply UV radiation to skin of a patient 1 to provide phototherapy to the patient. In at least one embodiment, the UV radiation is applied to affect controlled therapeutic modulation of an immune response by an immune system of the patient 1. FIG. 3A illustrates the application head 40 positioned to apply UV radiation to the skin on the chest of a patient 1 in locations that overlie the lungs of the patient 1, to treat a patient diagnosed with COVID-19, where the goal of the treatment is to modulate the immune response in the lungs, which are the target tissues in this embodiment. The apparatus and methods described herein can be used for phototherapy treatment for other diseases, including, but not limited to: hypertension, diabetes, cardiovascular disease, Graft versus Host Disease, Alzheimer's disease and other forms of dementia, stroke.

Figure 3B:
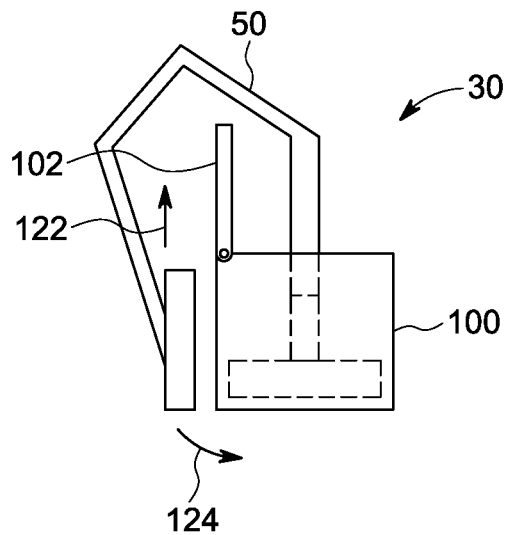
FIG. 3B illustrates the apparatus of FIG. 3A self-sterilizing the external surfaces of the housing and lid, according to an embodiment of the present invention.
Figure 3C:
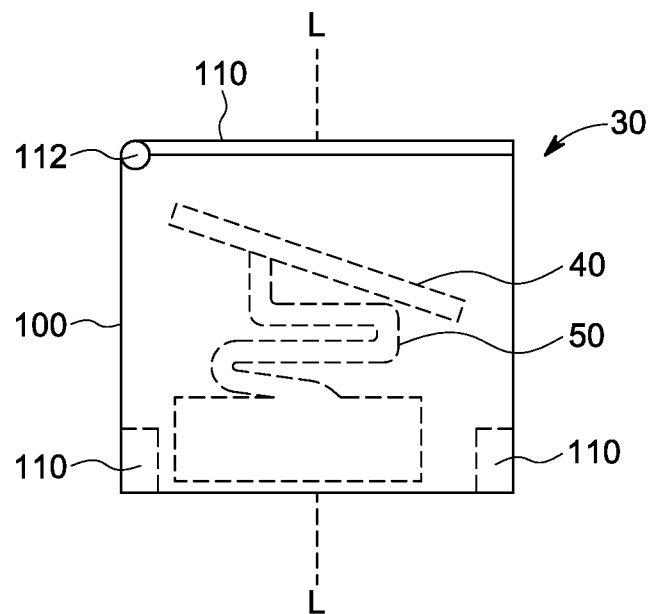
FIG. 3C illustrates the apparatus of FIG. 3A self-sterilizing the internal surfaces of the housing and lid and the external surfaces of the application head, articulating arm and base, according to an embodiment of the present invention.
Figure 3D:
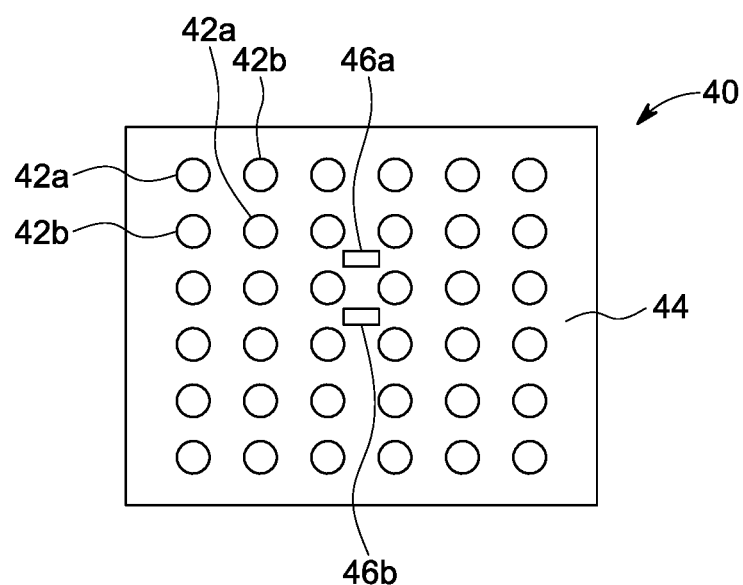
FIG. 3D illustrates a view of the application head of the apparatus of FIG. 3A.

FIG. 3D illustrates a front side view of the application head 40 showing the side from which the UV energy is emitted. Although fluorescent bulbs or incandescent bulbs could be used as the UV energy generating sources, it is preferred to use light emitting diodes (LEDs) and/or nanostructure UV light emitting devices as the UV energy generating sources, as these facilitate making the application head smaller and more portable, and also consume less energy and generate less heat than devices using fluorescent or incandescent bulbs. In the embodiment of FIGS. 3A-3D, the application head is substantially square, having a surface area configured to apply UV energy to skin overlying the area of the lungs. For example, the application head may have a length of about 1- to 14 inches and a width of about 10 to 14 inches. However, these dimensions are non-limiting of the invention, as the application head 40 dimensions may vary greatly, as they can be designed to cover a particular target area, defined by a surface of skin overlying a target underlying the skin that is to be treated. The embodiment shown in FIG. 3D includes LEDs 42a, 42b, as the UV emitting sources. In at least one embodiment, the LEDs 42a and 42b are the same and are both configured to emit the same wavelength or wavelength range of UVB energy. In another embodiment, LEDs 42a are LEDs designed to emit UVB energy and LEDs 42b are LEDs designed to emit UVC energy. In another embodiment, LEDs 42a are LEDs designed to emit UVB energy and LEDs 42b are LEDs designed to emit UVB energy having a different wavelength or wavelength range than the wavelength or wavelength range emitted by LEDs 42a. In at least one embodiment at least one of LEDs 42a or LEDs 42b are configured to emit NB-UVB radiation.

The wavelengths/wavelength ranges of radiation emitted for application to the skin of the patient may be any of the wavelengths described above with regard to FIGS. 1-2. One preferred wavelength ranges is NV-UVB (308 nm to 315 nm). The intensity and duration of the UV energy applied to the skin by apparatus 30 have already been described above.

UVB energy includes wavelengths between 280 nm and 315 nm. UVC energy includes wavelengths between 100 nm and 280 nm. When UVB is used for self-sterilization, the wavelengths/wavelength ranges of radiation emitted by application head 40 for self-sterilization of the apparatus 30 can be the same or different from those used for application to the skin of the patient 1. When UVC energy is used for self-sterilization, the wavelengths/wavelength ranges may be any wavelength or wavelength range between 100 nm and 280 nm. In some exemplary embodiments according to the present invention, a single wavelength can be 150 nm, 175 nm, 200 nm, 201 nm, 202 nm, 203 nm, 204 nm, 205 nm, 206 nm, 208 nm, 209 nm, 210 nm, 211 nm, 212 nm, 213 nm, 214 nm, 215 nm, 220 nm, 230 nm, 240 nm, 250 nm, 260 nm, 270 nm, or 280 nm, or any wavelengths therebetween. The wavelengths can include a range of about 100-280 nm, 150-160 nm, 190-194 nm, 195-199 nm, 200-204 nm, 205-209 nm, 210-214 nm, 215-218 nm, 219-223 nm, 224-230 nm, 230-235 nm, 240-250 nm, 270-280 nm, or ranges therebetween or subsets of these ranges.

Application of UV energy to the apparatus 30 by application head 40 to accomplish self-sterilization is a power density and geometry analysis. UVC LED lights may be within the chamber to provide a source of disinfection/sterilization. Additionally, if the chamber is UVB reflective, the light could be submersed and oriented to reflect the sterilization/disinfection energy source about the chamber. Power density output of about 7.0 to about 100 mW/cm$^2$ for a duration of 1 to 3 minutes seconds, typically within a range from 10 to 50 mW/cm$^2$ for a duration of 1 to 3 minutes.

LEDs 42a, 42b can be designed to emit a particular wavelength or wavelength range from sources such as Cree Inc. (USA), Nichia (Japan), Toyoda Gosei (Japan), Crystal IS (USA), Philips (USA). Selectable power supplies can be provided that control how and when various LEDs are powered when LEDs 42a, 42b that emit different wavelengths are employed. LEDs 42a, 42b can be mounted on a circuit board 44 that is mounted within the application head 40. In the embodiment of FIG. 3D, the circuit board 44 is flat, but in alternate embodiments, it could be curved or provided with some other surface conformation.

Optionally, a set of LEDs of a single LED type can be controlled with different junction currents and power duty cycles among the individual LEDs within the set of LEDs of a single LED type in order to broaden the spectral density of UV wavelengths emitted by the set as a whole. In addition, multiple sets of LEDs of differing types can be used to broaden the spectral density of UV wavelengths to a greater extent than is possible with a set of LEDs of a single type. The purpose of the manipulation of the LEDs is to be able to tailor the UV wavelength for a specific purpose such as irradiation of the skin for therapy, or irradiation of the apparatus to self-sterilize.

Apparatus 30 may be further provided with one or more sensors 46a, 46b to calibrate power and/or spectrum to maintain, adjust and report performance of the energy sources 42a, 42b for external or internally adjusted time or intensity adjustments to optimize treatment and or sterilization parameters. Additionally or alternatively, sensors may be configured to detect a distance of the application head from the skin of the patient and/or to sense the temperature of the patient and/or sense the respiration rate of the patient. Further additionally or alternatively, sensors may include geometric sensors to sense geometry of the surface of the target skin of the patient that is to be irradiated, for use of the sensed geometry in calculation a dose of radiation to be applied, as the dose of UV radiation is geometry dependent between patient and UV source.

Nanostructure UV energy emitting devices may be used in combination with LEDs 42a and/or 42b, or as a substitute for one or both types of these LEDs. A nanostructure UV energy emitting device may include at least one of a nanoparticle and a nanowire UV energy emitting device. In some embodiments, the UV energy emitting device emits only UVB. In other embodiments the UV energy emitting device emits only UVC. In still other embodiment, the UV energy emitting device can be controlled to emit UVB or UVC energy.

Nanoparticles may be any suitable nanoparticles, such as nanocrystals or quantum dots, for example. Metal, semiconductor, as well as metal or semiconductor oxide and/or nitride nanoparticles may be use. Semiconductor nanoparticles include materials from Groups IV (Si, Ge, SiC, SiGe), II-VI (CdS, ZnS, CdSe, ZnSe, ZnTe, CdTe), IV-VI (PbS, PbSe, PbTe) or III-V (GaAs, GaP, GaN, InP, InAs). Ternary and quaternary semiconductor nanoparticles, such as CdZnS, CdZnSe, CdZnTe, CdZnTeSe, CdZnSSe, GaAlAs, GaAlP, GaAlN, GaInN, GaAlAsP and GaAlInN for example, may also be used. Ceramic or metal oxide nanoparticles may also be used, such as silica, alumina, titania, zirconia, yttria stabilized zirconia, yttria, ceria, spinel (for example, $MgO*Al_2O_3$) and tantalum pentoxide, as well as other suitable ceramics having a more complex structure, such as radiation emitting phosphors (for example, YAG:Ce ($Y_3Al_5O_{12}$:Ce) and various halophosphate, phosphate, silicate, aluminate, borate and tungstate phosphors) and scintillators (for example, LSO, BGO, YSO, etc.). Other metal oxide nanoparticles, such as aluminum nitride may also be used. Metal nanoparticle may be pure metal or metal alloy nanoparticle, such as Al, Fe, Cu, Ni, Au, Ag, Pt, Pd, Ti, V, Ta, W, Mn, Zn, Mo, Ru, Pb, Zr, etc. and alloys thereof.

Other materials, such as Boron Carbide, Titanium Oxide (TiO), Silicon Carbide (SiC), Antimony (Sb), Arsenic (As), Bismuth (Bi), Cadmium (Cd), Carbon (C), Gallium (Ga), Germanium (Ge), Indium (In), Phosphorus (P), Selenium (Se), Sulfur (S), Tellurium (Te), Calcium (Ca), Chromium (Cr), Cobalt (Co), Magnesium (Mg), Tantalum (Ta), Silicon Arsenide Germanium Telluride (SiAsGeTe), Vanadium Oxide, Zinc Germanium Phosphide (ZnGeP2), Zinc Germanium Phosphide (ZnGeP), Aluminum Antimonide (AlSb), Aluminum Arsenide (AlAs), Aluminum Phosphide (AlP), Gallium Selenide (GaSe), Gallium Telluride (GaTe), Indium Antimonide (InSb) and Silicon Arsenide Telluride (SiAsTe) may also be used.

Nanoparticles may be provided in the UV emitting application head 40 in any suitable form. For example, the nanoparticles may be located as a solid layer or layers on a UV transparent and UV resistant material substrate. The solid layer may also contain a UV transparent and UV resistant binder or filler if desired. Alternatively, the nanoparticles may be located in a suspension. The fluid of the suspension may comprise any suitable UV transparent fluid. Preferably, the fluid comprises a fluorocarbon fluid, such as perfluorocarbon, chlorofluorocarbon or hydrofluorocarbon fluid. For example, the fluid may comprise 1,1,1,2 tetrafluoroethane also known as R134A or perfluorocarbon fluids sold under the PPx series from F2 Chemicals Ltd. in Lea Town, U.K., such as the PP6 perfluorocarbon fluid. The R134A fluid is provided under elevated pressure to remain in the liquid state at room temperature. Other fluids which are liquid at atmospheric pressure at room temperature may also be used. If the nanoparticles are located in as suspension, then the suspension is located in a sealed vessel or tube made of a UV transparent and UV resistant material. If desired, the device (4) may also contain a pump or vibrator which maintains the suspension under turbulent flow to prevent the nanoparticles from settling on the surface of the vessel.

Nanowires may be any suitable nanowires and may comprise any suitable material, such as metal oxide material. For example, zinc oxide, indium oxide and indium tin oxide nanowires may be used. Any suitable length of nanowires may be used. A UV excitation source can be used to cause the nanostructure UV energy emitting device to emit UV energy. Further details regarding making an apparatus that employs a nanostructure UV energy emitting device can be found in US Patent Application Publication No. 2015/0025601 A1, which is incorporated herein, in its entirety, by reference thereto.

The application head 40 is mounted to one end of articulating arm 50. The other end of articulating arm 50 is connected to a base 60 that sits in or is mounted to the bottom of housing 100. The articulating arm 60 may be articulated either manually or automatically to orient the application head in a desired position. In the embodiment of FIG. 3A, application head 40 has been oriented to interface with the skin of the patient 1 at a location that overlies the lungs. This orientation can be arrived at through manual adjustment as noted. Alternatively, a display 80 may be provided that can be operated by a user to control a drive system configured to articulate the articulating arm 60 in a three-dimensional space. The display may be integrated with the housing 100 and/or hardwired to the controller for controlling the articulating arm 60, but is preferably wirelessly connectable to the controller, as the display 80 would then not need to be subjected to the self-sterilization process, but could be cleaned separately.

The application head 40 can be placed at a known distance from the patient 1, such as positioned adjacent to and facing the skin but separated by a predetermined distance such as 8 to 12 inches or some other predefined distance. The body surface target and beam spread of the light source will determine the geometry.

As clinical dosage is a function of geometry, the articulation head 40 can also be configured to have a means of controlling the geometry to improve dose management. For example, a physical cone almost body contacting or an electronic/non-contacting range finder internal or external to the application head/source 40 can be used to manage distance.

The distance from the skin will affect the intensity of the UV radiation applied to the skin, but this can be compensated for to standardize the treatment by calculations using input from the sensors 46a, 46b.

Base 60 may house a power source 62 such as a battery, that powers the UV emitting sources in the application head 40 as well as any motors and controllers used in the apparatus. Alternatively, a power cord 63 could be used to provide power by plugging into a wall outlet, but this is less preferred as it provides additional complications for sterilization.

Apparatus 30 may also be provided with one or more processors 70 that can be powered by power source 62,63 to control application of UV radiation to the skin of the patient via the application head 40, and to control application of UV radiation to the apparatus 30 via the application head 40 to perform self-sterilization.

One or more motors 82 may be operatively connected to move the articulating arm into desired configurations within a three-dimensional range of its movement capabilities. The motor(s) maybe powered by the power source 62, 63 and controlled via the processor 70 automatically and/or controlled manually via input through display 80.

FIG. 3B illustrates the apparatus 30 of FIG. 3A self-sterilizing the external surfaces of the housing 100 and lid 110, according to an embodiment of the present invention. After the external surfaces have been sterilized via application of UVB and/or UVC radiation to the surfaces thereof, for a predetermined time and dosage per square centimeter of surface, the apparatus can then be controlled (either manually, or, more preferably is programmed for automatic movements) to fully retract the application head 40 and articulating arm 50 into the housing 100 as illustrated in FIG. 3C, and the lid 110 is closed (preferably automatically by a motor driven process, or, manually). The application head 40, articulating arm 50 and optionally base 60 can then be controlled to apply UVC and/or UVB radiation for sterilization of the internal surfaces of the housing 100 and lid 110, as well as the external surfaces of the application head 40, articulating arm 50 and base 60. FIG. 3C illustrates the apparatus of FIG. 3A self-sterilizing the internal surfaces of the housing 100 and lid 110 and the external surfaces of the application head 40, articulating arm 50 and base 60, according to an embodiment of the present invention.

Figure 3E:
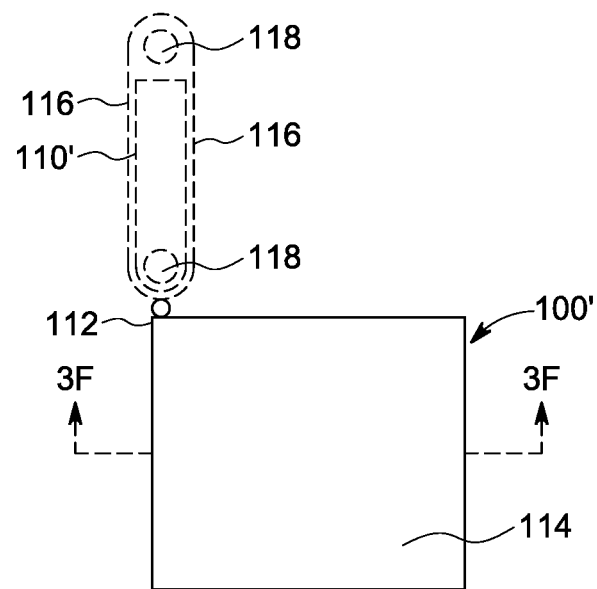
FIG. 3E illustrates a housing that can be used as an alternative to the housing of FIG. 3A, according to an embodiment of the present invention.
Figure 3F:
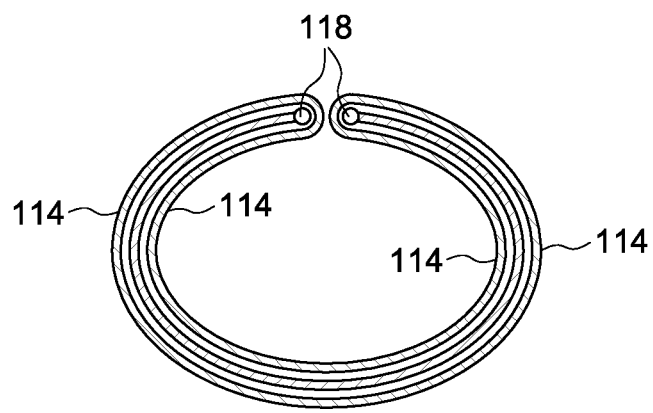
FIG. 3F is a cross-sectional view of FIG. 3E taken at 3F-3F.
Figure 3G:
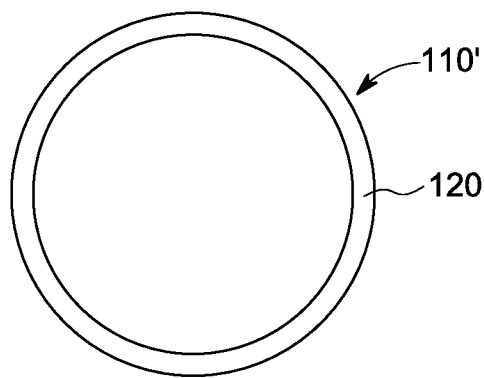
FIG. 3G is a cutaway view of the housing of FIG. 3E.

FIG. 3E illustrates a housing 100' that can be used as an alternative to the housing 100 for the apparatus 30, according to an embodiment of the present invention. A lid 110' may optionally be provided. In this embodiment, the surfaces 114 of the housing 100' (as well as the lid 110' when used) are mirrored surfaces so that they readily reflect UV energy applied thereto. The surfaces 114 and 116 are configured so that they can be rolled by motor-driven rollers 118 so as to be driven from positions inside the housing 100' (or lid 110') to outside the housing 100' (or lid 110'). FIG. 3E shows that the optional lid 110' has a continuous sheet or film 116 that loops over the motor-driven rollers and is engaged therewith so as to be driven by the rollers 118. Likewise, the cross-sectional view in FIG. 3F shows that the housing 100' has a continuous sheet or film 114 that loops around the motor-driven rollers 118 and is engaged thereby so as to advance the sheet or film similar to advancing a movie film or microfilm. In this way, both internal and external surfaces of the housing 100' (and, optionally, lid 110') can be sterilized by application of UV radiation from the application head 40 when it is located inside the housing 100' (in a similar position to that shown in FIG. 3C). Because the surfaces of the housing 100', lid 110' can be moved into and out of the path of the application of UV at a controlled rate, a controlled dosage can be delivered using a controlled intensity and a controlled advancement rate of the surface 114. FIG. 3G is a cutaway view of the housing 100' of FIG. 3E that shows a channel 120 that can be formed at the bottom of the housing, in which the film or sheet 114 can be guided when it is driven by the motorized rollers. A similar channel can be provided at the top of the housing 100'

Figure 3H:
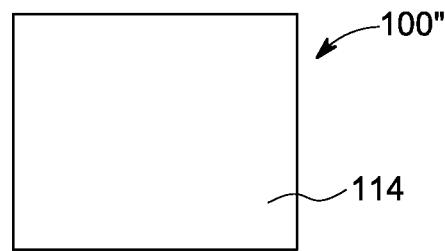
FIG. 3H illustrates a housing that can be used as an alternative to the housings of FIG. 3A and FIG. 3E, according to an embodiment of the present invention.
Figure 3I:
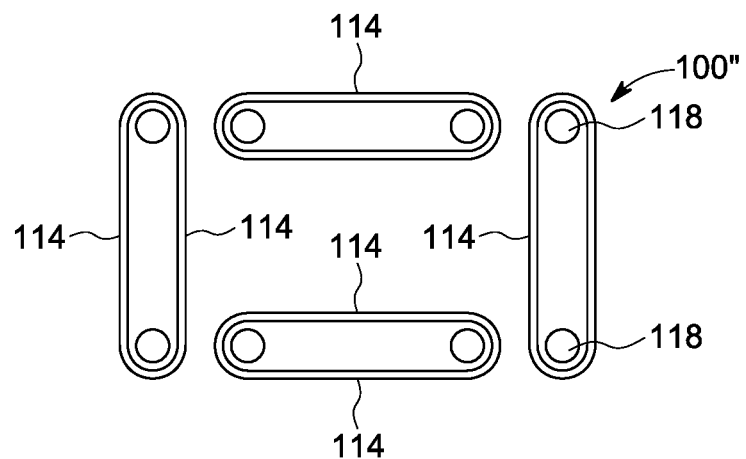
FIG. 3I is a schematic illustration of a top view of the housing of FIG. 3H.

FIG. 3H illustrates a housing 100" that can be used as an alternative to the housings 100, 100' for the apparatus 30, according to an embodiment of the present invention. A lid 110' may optionally be provided, like that in the embodiment of FIG. 3E and is not shown in FIG. 3H. In this embodiment, the housing is not circular or cylindrical, but rather square or rectangular in cross section, as also shown in the top view illustration of FIG. 3I. Because of this surfaces 114 of the housing 100" are flat, rather than curved (except for where they are driven around the rollers 118). Thus four sets of rollers 118 are provided to drive the films or sheets 114 of the four sides of the housing 100". Although the films or sheets 114 are driven horizontally in the embodiment of FIGS. 3H-3I, they could, alternatively be driven vertically.

The apparatus 30 may be provided with wheels 110 that permit the apparatus to be moved by wheeling it along the floor surface, such as by pushing or pulling it. Alternatively, wheels 110 can be operatively connected to one or more motors 82 via a drive train (not shown) so that the apparatus can be self-driven. Control of the driving may be afforded to the user through operation of the display 80.

Figure 4:
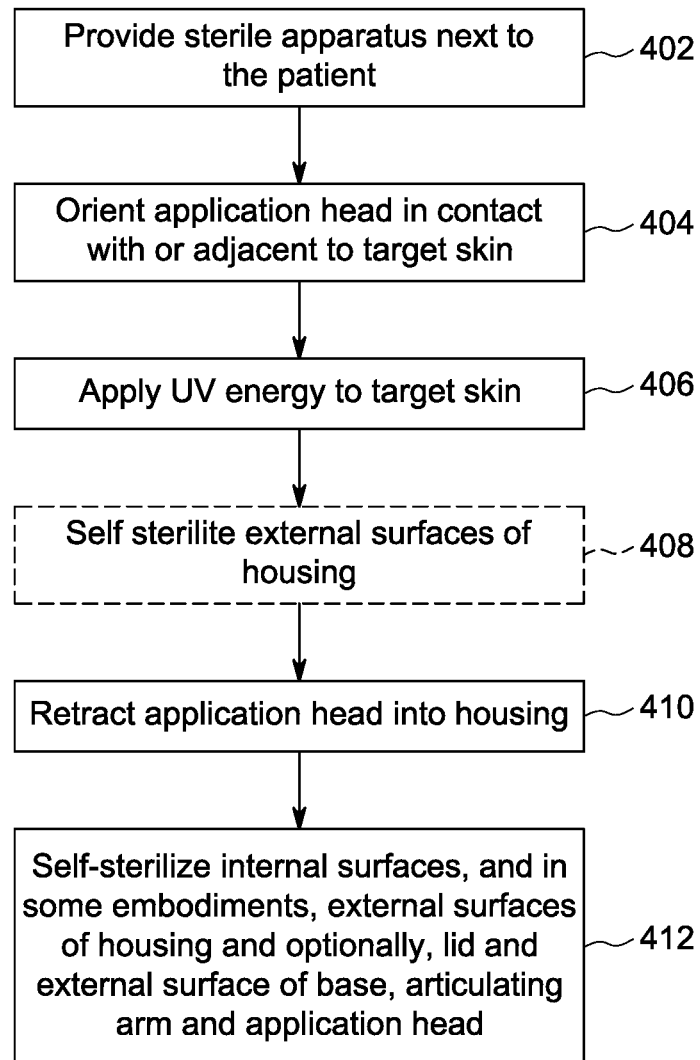
FIG. 4 illustrates events that may be carried out during use of an apparatus to provide a phototherapy treatment to a patient at a location of the patient such that the patient does not need to be brought to a location where a fixed UV apparatus is located, according to an embodiment of the present invention.

FIG. 4 illustrates events that may be carried out during use of apparatus 30 to provide a phototherapy treatment to a patient at a location of the patient such that the patient does not need to be brought to a location where a fixed UV apparatus is located. A clean, sterile apparatus is transported to the room that the patient is located in, whether it be in the ICU, a private hospital room, an outpatient clinic, or other location. Prior to beginning the phototherapy, the apparatus can optionally be sterilized, if it has not already been sterilized, using a self-sterilization technique described herein, or any other suitable sterilization technique. The sterile, stand-alone apparatus is thus placed next to a patient 1 at event 402.

At event 404, the application head 40 is oriented so that it is in a correct position to apply UV radiation directly to the skin (target skin) of the patient 1 that overlies the target tissue where it is desired to focus activation of immune regulation. For example, when treating a COVID-19 patient, the application head may be oriented to apply UV radiation directly to the skin on the chest of the patient 1 that overlies the lungs. Orientation may be performed by manipulating the articulating arm 50 manually, or automatically such as by controlling one or more motors 82 using display 80 via processor 70.

At event 406, UV energy is emitted from application head to the target skin for a predetermined time period to deliver a predetermined dose of radiation. After the predetermined time has passed and the predetermined dose of radiation has been delivered, the processor 70 controls the application head 40 to cease emission of UV radiation and the application head is moved away from the patient. Optionally, at event 408 the apparatus may perform a self-sterilization of the external surfaces of the housing, including the external surface of the lid 102. The processor 70 may be preprogrammed to translate 122 and rotate 124 the application head 40 (see FIG. 3B) along a predefined pattern at a predefined (constant or variable) speed to ensure that the radiation (UVB and/or UVC) is applied in sufficient dose across all external surface area of the housing 100 and lid 102 sufficient to sterilize the same.

Next, the processor 70 controls the articulating arm 50 to retract the application head 40 completely into the housing 100 and orient it in a proper orientation so that the entire interior of the housing and the exterior surfaces of the base 60, articulating arm 50 and application head 40 can be sterilized. In embodiments where the apparatus has a lid 110, 110', the processor 70 is also operatively connected to a motor 112 that it controls to open or close lid 110, 110'. After the application head 40 has been completely received into the housing 100, the processor 70 controls the lid motor 112 to close the lid for embodiments that have a lid, as shown in FIG. 3C. The inner walls of the housing 100 and lid 110 are mirrored surfaces so that they readily reflect UV energy applied thereto. At event 412, the processor 70 activates the application head 40 to emit UV radiation that is configured to self-sterilize the apparatus. The UV energy is reflected off the mirrored surfaces and contacts all surfaces of the inner walls of the housing 100 and lid 110, as well as all external surfaces of the base 60, articulating arm 50 and application head 40. In the embodiments of FIGS. 3E and 3H, the walls 114 (and optionally, walls 116) are driven so that both internal and external surfaces of the housing 100', 100" (and optionally of the lid 110') are moved inside the housing so that both internal and external surfaces are sterilized by all surfaces being exposed to UV within the housing 100', 100" for predetermined times and dosages to effectively sterilize both inside and outside walls of the housing. The processor 70 may be preprogrammed to operate the application head 40 for a time and at an intensity and frequency to ensure that all the mentioned surfaces have been sufficiently irradiated so as to be sterilized. Optionally, the base 60 may be mounted on a motorized turntable operable by processor 70 to rotate it (and therefor also the application head 40) about the longitudinal axis L-L of the housing 100, thereby further enhancing the overlapping and covering by the UV radiation on the surfaces being sterilized.

Figure 5:
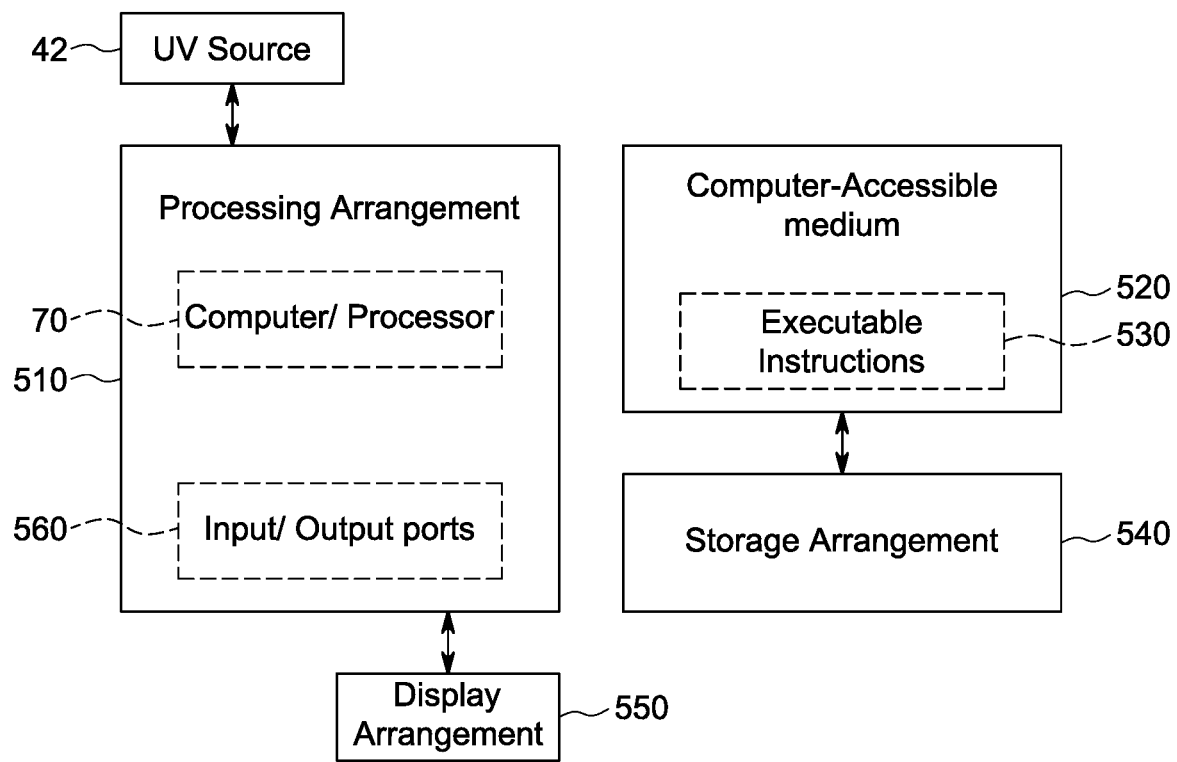
FIG. 5 shows an exemplary block diagram of an exemplary embodiment of a system according to an embodiment of the present invention.

FIG. 5 shows an exemplary block diagram of an exemplary embodiment of a system according to an embodiment of the present invention. For example, exemplary procedures in accordance with the present disclosure described herein can be performed by or controlled using a UV source 42 such as LEDs and/or nano-structure UV emitting device and/or fluorescent tubes or incandescent tubes and/or hardware processing arrangement and/or a computing arrangement 510, separately and in conjunction with one another. Such exemplary processing/computing arrangement 510 can be, for example, entirely or a part of, or include, but not limited to, a computer/processor 70 that can include, for example, one or more microprocessors, and use instructions stored on a computer-accessible medium (e.g., RAM, ROM, hard drive, or other storage device).

A computer-accessible medium 520 (e.g., as described herein above, a storage device such as a hard disk, floppy disk, memory stick, CD-ROM, RAM, ROM, etc., or a collection thereof) can be provided (e.g., in communication with the processing arrangement 510). The computer-accessible medium 520 can contain executable instructions 530 thereon. In addition or alternatively, a storage arrangement 540 can be provided separately from the computer-accessible medium 520, which can provide the instructions to the processing arrangement 510 so as to configure the processing arrangement to execute certain exemplary procedures, processes and methods, as described herein above, for example.

Further, the exemplary processing arrangement 510 can be provided with or include an input/output arrangement 560, which can include, for example, a wired network, a wireless network, the internet, an intranet, a data collection probe, a sensor, etc. The exemplary processing arrangement 510 can be in communication with an exemplary display arrangement 550, which, according to certain exemplary embodiments of the present disclosure, can be a touch-screen configured for inputting information to the processing arrangement in addition to outputting information from the processing arrangement, for example. Further, the exemplary display 550 and/or a storage arrangement 540 can be used to display and/or store data in a user-accessible format and/or user-readable format.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

For example, acute and chronic photo-immune response may provide a mechanism of acute and chronic impact for the clinical good. A method of controlled therapeutic modulation of the immune response by UV light to reduce the acute clinical condition, cytokine release system and cytokine storm, an over-reaction of the immune system, as is seen in numerous auto-immune disorders including GVHD and the coronavirus can be provided.

The apparatus as disclosed herein can be used for controlled therapeutic modulation and correction of immune dysregulation of the immune response by UV light.

A method of prophylactically delivering a chronic and/or repeating regimen of UV phototherapy can be provided to reduce neuro-inflammation associated with maladies including but not limited to, dementia, Alzheimer's and neurocognitive decline. For example, a semi-annual regimen for re-synchronizing the immune system could be provided that would be less invasive than recurring dental visits.

Apparatus are provided for controlled therapeutic modulation and correction of immune dysregulation of the immune response by UV light and blood chemistry analysis as a closed loop to optimize treatment.

Alternative embodiments to the stand-alone version of the self-sterilizing apparatus may be provided. For example, for external surfaces, the UV emitting lights and or external surfaces may rotate to provide surface exposure to the sterilizing radiation (e.g. a UVC source). The exposed components may also be manufactured from UVC transmitting materials to provide complete surface sterilization from the UVC surfaces.

In an embodiment, all of the UV emitters (lights) and exposed surfaces are fixed in a cabinet. A further embodiment is the translation of the UVC sources to the relevant surfaces in the form of a rotating gantry or other mechanically controlled translating arm. Another embodiment is to provide the surface be have integrated UVC sources for direct sterile dose.

Confirmation of sterilization can integrated with terrain mapping of the mechanism surface and dose calculations tracking distance and power output to achieve acceptable dosage.

It is common in the art for UVB to be delivered with bulbs as well as with LED and they are considered in this disclosure to be interchangeable. The vision of tunable bulbs and LEDs is also envisioned in this disclosure.

Another embodiment provides a reflective surface or waveguide to be translated about the surfaces of the unit to distribute coverage of the sterilizing energy.

In all embodiments, the system for UVB and/or UVC may have integrated sensors to calibrate power and/or spectrum to maintain, adjust and report performance of the energy sources for external or internally adjusted time or intensity adjustments to optimize treatment and or sterilization parameters.

That which is claimed is:

1. A method of controlled therapeutic modulation of an immune response by an immune system of a patient, said method comprising:
   testing patient biological feedback to establish a baseline level of one or more indicators of immune regulation;
   applying UV radiation to skin of the patient for a predetermined time period or dose;
   repeating said applying step for said predetermined time period or dose, or for a modified predetermined time period or dose based on patient feedback after said applying for said predetermined time period or dose, multiple times, wherein each said repeating treatment is performed after a predetermined rest period;

retesting the patient after at least one session of said applying UV radiation;

comparing levels of said one or more indicators determined in said retesting to levels established as said baseline levels;

discontinuing said repeating said applying step for said predetermined or modified predetermined time period or dose when a predetermined differential threshold between said retesting levels and said baseline level in at least one of said one or more indicators has been met; and further repeating said applying step for said predetermined time period or dose or modified predetermined time period or dose when said differential threshold has not been met, said further repeating steps being carried out until said differential threshold has been met, or for a predetermined number of times, whichever occurs first.

2. The method of claim 1, wherein said one or more indicators include T-cells and cytokines.

3. The method of claim 1, wherein said one or more indicators include at least one of temperature, heart rate, and blood oxygen levels.

4. The method of claim 1, wherein said testing further includes testing for a Vitamin D level.

5. The method of claim 1, wherein said one or more indicators comprise inflammatory markers including at least one of CRP, LDH and ferritin, and wherein said method further comprises discontinuing said repeating said applying step for said predetermined time when a predetermined inflammatory differential threshold between a retesting level of at least one of said inflammatory markers and said baseline level of said at least one of said inflammatory markers has been met.

6. The method of claim 1, wherein said applying UV radiation comprises applying UVB radiation.

7. The method of claim 1, wherein said applying UV radiation comprises applying a combination of UVC and UVB radiation.

8. The method of claim 1, wherein said applying UV radiation comprises applying NB-UVB radiation.

9. The method of claim 1, wherein the patient has a cognitive disorder, such as dementia or Alzheimer's disease and the method is applied to improve outcomes for the patient's cognitive disorder.

10. The method of claim 1, wherein the patient is has an infection of coronavirus/COVID-19 and the method is applied to improve outcomes for the coronavirus/COVID-19 patient.

11. The method of claim 1, wherein the patient has an infection of sepsis and the method is applied to improve outcomes for the sepsis patient.

12. The method of claim 1, wherein the method is applied to the patient in an acute setting.

13. The method of claim 12, wherein the method is applied to the patient in an intensive care unit (ICU).

14. The method of claim 1, wherein the patient has at least one of hypertension, diabetes, cardiovascular disease, and/or stroke.

15. The method of claim 1, wherein the patient has an infection of a coronavirus and the method is applied to improve outcomes for the coronavirus patient.

* * * * *